United States Patent
Gazala et al.

(10) Patent No.: US 10,507,667 B2
(45) Date of Patent: Dec. 17, 2019

(54) SYSTEM AND METHODS FOR DETECTING MALFUNCTIONING NOZZLES IN A DIGITAL PRINTING PRESS

(71) Applicant: ADVANCED VISION TECHNOLOGY (A.V.T.) LTD, Hod Hasharon (IL)

(72) Inventors: Chanan Gazala, Kfar Saba (IL); Gilad Golan, Netanya (IL); Barry Ben Ezra, Ramat Hasharon (IL); Dan Zamir, Hod Hasharon (IL)

(73) Assignee: Advanced Vision Technology (A.V.T.) Ltd., Hod Hasharon (IL)

(*) Notice: Subject to any disclaimer, the term of this patent is extended or adjusted under 35 U.S.C. 154(b) by 0 days.

(21) Appl. No.: 15/771,056

(22) PCT Filed: Oct. 26, 2016

(86) PCT No.: PCT/IL2016/051151
§ 371 (c)(1),
(2) Date: Apr. 25, 2018

(87) PCT Pub. No.: WO2017/072760
PCT Pub. Date: May 4, 2017

(65) Prior Publication Data
US 2018/0319175 A1    Nov. 8, 2018

Related U.S. Application Data

(60) Provisional application No. 62/412,510, filed on Oct. 25, 2016, provisional application No. 62/246,154, filed on Oct. 26, 2015.

(51) Int. Cl.
*B41J 2/21* (2006.01)
*B41J 29/393* (2006.01)

(52) U.S. Cl.
CPC ......... *B41J 2/2142* (2013.01); *B41J 2/2146* (2013.01); *B41J 29/393* (2013.01); *B41J 2029/3935* (2013.01)

(58) Field of Classification Search
CPC ...... B41J 2/2142; B41J 2/2146; B41J 29/393; B41J 2029/3935
See application file for complete search history.

(56) References Cited

U.S. PATENT DOCUMENTS 6,637,853 B1  10/2003  Ahne et al.
8,363,261 B1  1/2013  Zimmerman
(Continued)

FOREIGN PATENT DOCUMENTS

JP    2006240148 A    9/2006

OTHER PUBLICATIONS

IP.com search (Year: 2019).*
(Continued)

*Primary Examiner* — Lisa Solomon
(74) *Attorney, Agent, or Firm* — RatnerPrestia

(57) ABSTRACT

A method identifies at least one malfunctioning nozzle in a digital printing press, the digital printing press including a plurality of nozzles. The method includes printing a design on a substrate, acquiring at least one image of the printed design and identifying at least one artifact in the acquired image. The method further includes identifying the malfunctioning nozzle and classifying the at least one malfunctioning nozzle according to the at least one of the acquired image of the printed design, at least a portion of a nozzle pattern and at least a portion of a uniformity pattern.

18 Claims, 10 Drawing Sheets

(56) References Cited

U.S. PATENT DOCUMENTS

2012/0194600 A1  8/2012  Kido
2012/0293817 A1  11/2012 Kasai
2014/0232772 A1  8/2014  Sasaki et al.

OTHER PUBLICATIONS

International Search Report for PCT/IL2016/051151, dated Feb. 19, 2017.
Extended European Search Report for European Application No. 16 859 201.2, dated May 23, 2019, 13 pages.

* cited by examiner

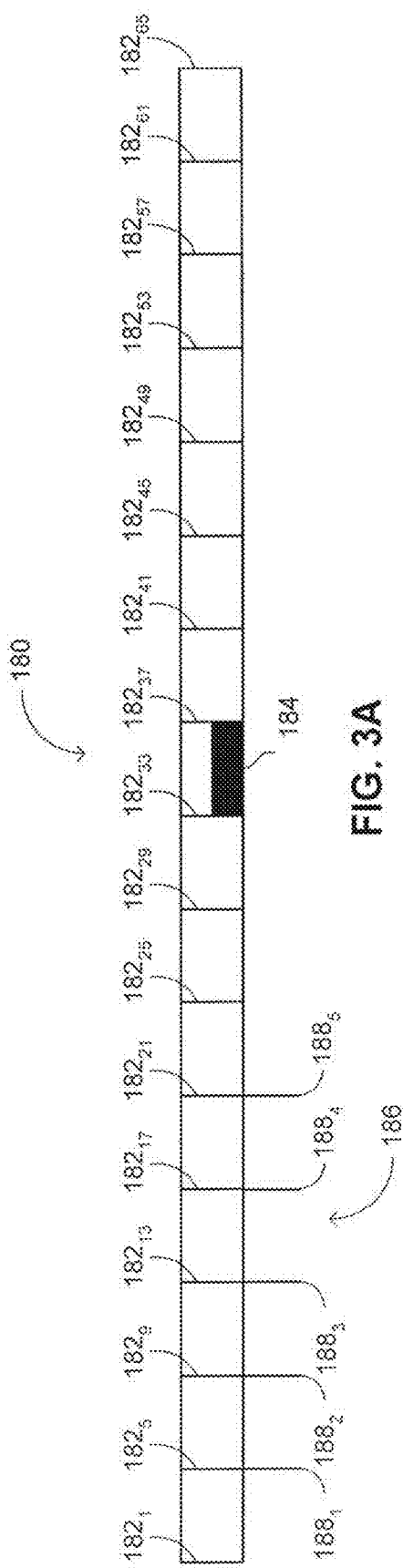
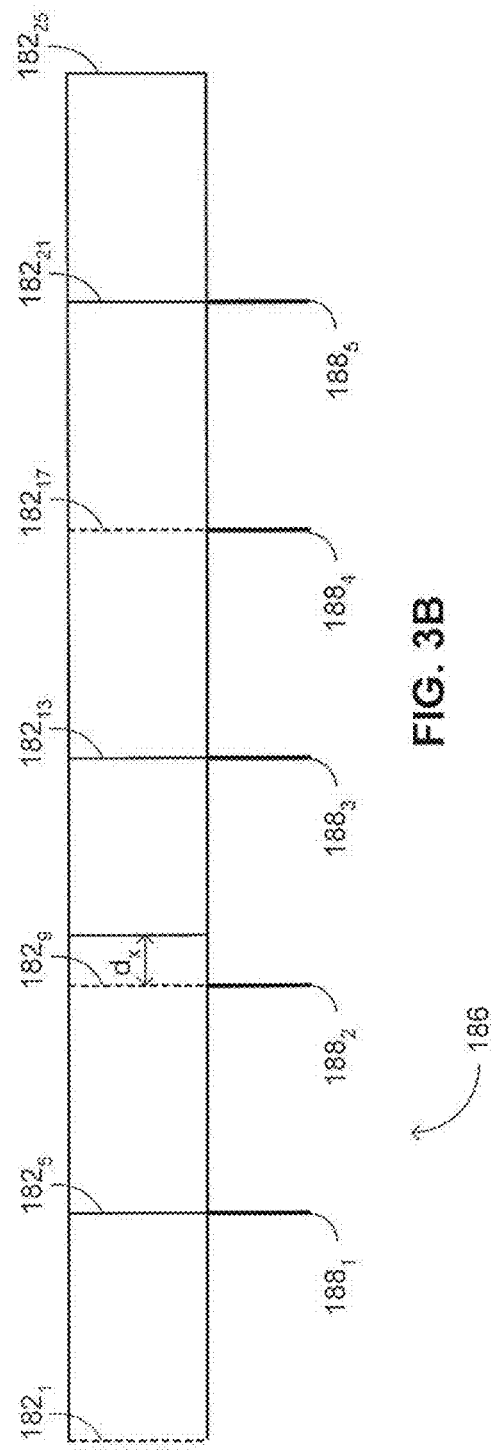
FIG. 3A
FIG. 3B

SYSTEM AND METHODS FOR DETECTING MALFUNCTIONING NOZZLES IN A DIGITAL PRINTING PRESS

This application is a National Stage application of PCT/IL2016/051151, filed 26 Oct. 2016, which claims priority to U.S. Provisional Patent Application No. 62/246,154, filed 26 Oct. 2015, and U.S. Provisional Patent Application No. 62/412,510, filed 25 Oct. 2016, which applications are incorporated herein by reference. To the extent appropriate, a claim of priority is made to each of the above-disclosed applications.

FIELD OF THE DISCLOSED TECHNIQUE

The disclosed technique relates to printing presses in general, and to methods and system for detecting malfunctioning nozzles in a digital printing press, in particular.

BACKGROUND OF THE DISCLOSED TECHNIQUE

Digital printing presses in general and ink jet based printing presses in particular (e.g., printing sheets or of labels) are required to print a print job continuously and with minimum waste. Waste is defined as printed material which is not sellable, substrate which is used to print the printed design (i.e., the product) and thus does not generate revenue generation and the like. Ink jet nozzles have some probability of malfunctioning. The results of such a malfunction may vary. In some cases the results of such a malfunction may be substantial and noticeable in the printed image (i.e., and thus affect the sellability of the product), while in other cases the result in such a malfunction may not be noticeable (i.e., and thus not affect the sellability of the product). A digital printing press can attempt to rectify such malfunctioning nozzles when information relating to which nozzle or nozzles (e.g., nozzle number and color) malfunctioned is available.

U.S. Pat. No. 6,637,853 to Jude Ahne et al directs to a system for detecting faulty nozzles in an ink jet printer which includes having a plurality of ink jet nozzles. The system includes a host computer and an ink jet printer and an optical sensor. The host computer generates a test pattern that is printed on a print medium. The test pattern consists of multiple test images printed in a vertical stack relative to a reference position. A start bar is printed at the reference position. Each of the test images is printed by a separate nozzle on a print head of the printer, such that there is a test image corresponding to each nozzle. For a print head having several hundred nozzles, more than one page of the print medium will be required to complete the pattern. Each page on which the pattern is printed includes a start bar at the top. If a nozzle malfunctions, there will be no test image printed corresponding to that nozzle, resulting in an empty location. The optical sensor is used to inspect the test pattern to detect any empty locations. The position of an empty location correlates to the faulty nozzle that should have printed a test image in the empty location. The host computer uses this information to modify the print data that is sent to the printer in the future.

SUMMARY OF THE PRESENT DISCLOSED TECHNIQUE

It is an object of the disclosed technique to provide a novel method and system for identifying malfunctioning nozzles in a digital printing press. In accordance with the disclosed technique, there is thus provided a method of identifying at least one malfunctioning nozzle in a digital printing press, the digital printing press including a plurality of nozzles. The method includes the procedures of printing a design on a substrate, acquiring at least one image of the printed design and identifying at least one artifact in the acquired image. The method further includes the procedure of identifying the malfunctioning nozzle and classifying the at least one malfunction nozzle according to the at least one of the acquired image of the printed design, at least a portion of a nozzle pattern and at least a portion of a uniformity pattern.

In accordance with another aspect of the disclosed technique, there is thus provided a method of identifying at least one malfunctioning nozzle in a digital printing press. The digital printing press includes a plurality of nozzles. The method includes the procedures of printing at least one of at least a portion of a nozzle pattern and at least a portion of a uniformity pattern and acquiring at least one image of the at least one of at least a portion of the nozzle pattern and at least a portion of the uniformity pattern. The method further includes the procedure identifying the malfunctioning nozzle and classifying the at least one malfunction nozzle according to the at least one acquired image of the at least one of the at least a portion of the nozzle pattern and the at least a portion of the uniformity pattern.

BRIEF DESCRIPTION OF THE DRAWINGS

The disclosed technique will be understood and appreciated more fully from the following detailed description taken in conjunction with the drawings in which:

FIGS. 3A, 3B and 3C, are schematic illustrations of a single nozzle pattern row, in accordance with a further embodiment of the disclosed technique;

DETAILED DESCRIPTION OF THE EMBODIMENTS

The disclosed technique overcomes the disadvantages of the prior art by providing a system and methods for identifying a malfunctioning nozzle or a group of nozzles as well as classifying the malfunction. According to the disclosed technique, a malfunctioning nozzle is identified by printing one or both of a nozzle pattern and a uniformity pattern. The nozzle pattern enables detection at least one of missing nozzles, deviated nozzles, inconsistent nozzles and redundant nozzles. Such nozzles may cause streaks to appear on the printed design. The uniformity pattern enables detection of a nozzle or group of nozzles which deposit more or less ink than intended resulting in shades of the color being printed across the substrate rather than a uniform color. The term 'nozzle' relates herein to a discrete ink deposition unit which deposits a dot of ink on a substrate. The term 'identifying a malfunctioning nozzle' or 'identifying a nozzle' relates to identifying the location of the nozzle in a nozzle array. The term 'location of the nozzle' or 'nozzle location' relates to the location of the nozzle (e.g., the index number, bus address and the like) in the array of nozzles.

Figure 1:
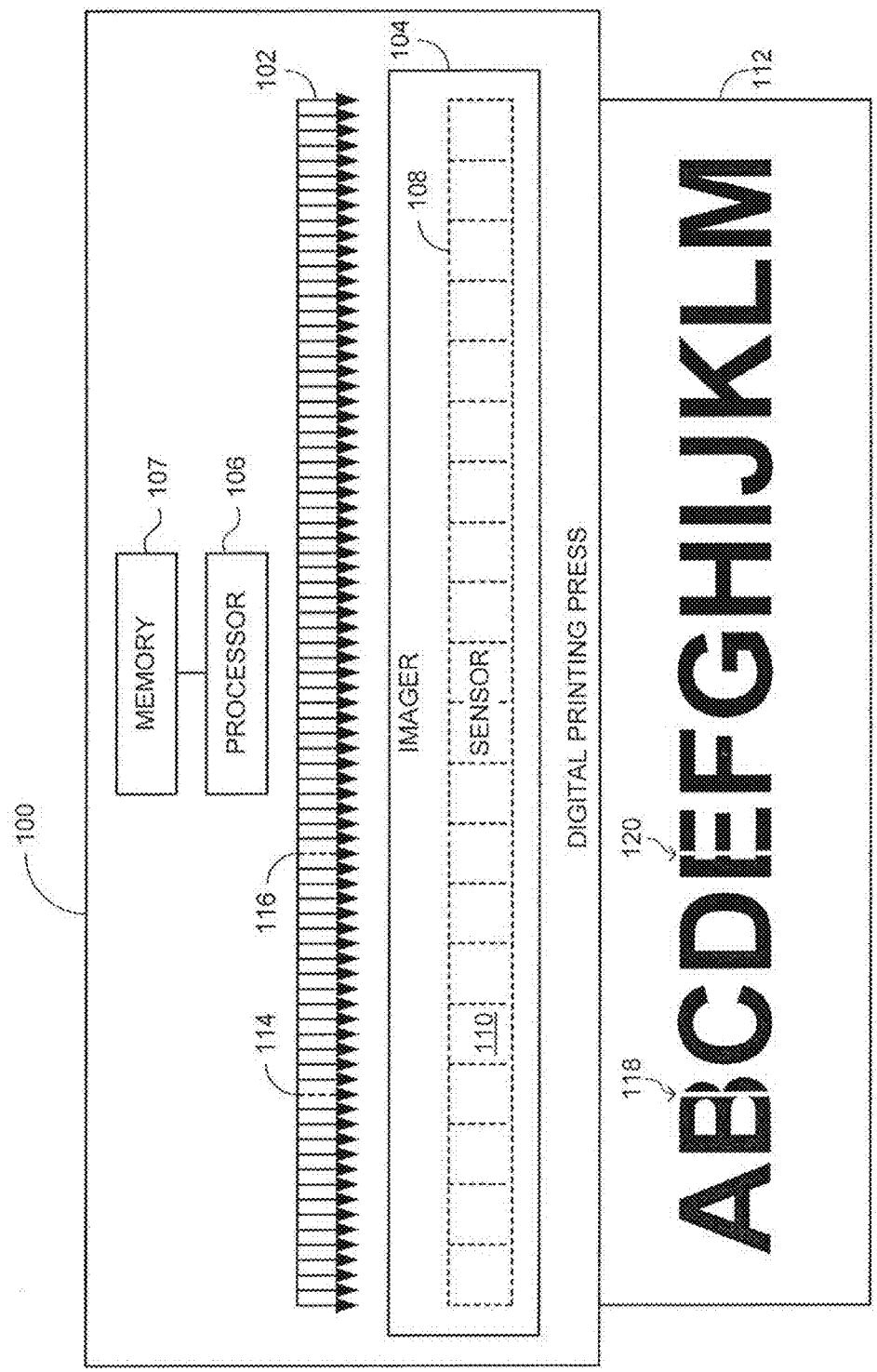
FIG. 1 is a schematic illustration of a digital press, with malfunctioning nozzle detection, constructed and operative in accordance with an embodiment of the disclosed technique.

Reference is now made to FIG. 1, which is a schematic illustration of a digital press, generally referenced 100, with malfunctioning nozzle detection, constructed and operative in accordance with an embodiment of the disclosed technique. Printing press 100 includes a nozzle bank 102, an imager 104, a processor 106 and a memory 107. Imager 104 includes a sensor 108. Sensor 108 includes a plurality of pixels sensors such as pixels 110. Processor 106 is coupled with nozzle bank 102, with memory 107 and with imager 104.

Imager 104 is for example a line-scan camera (i.e., which includes a line of pixel sensors) or a contact imager sensor (CIS) which acquires a grey level image or a color image (e.g., a Red Green and Blue—RGB image). Imager 104 may also be an area camera (i.e., which includes a matrix of pixel sensors). When imager 104 is a color imager, imager 104 includes an acquisition channel (e.g., at least one line of sensors or at least one respective illumination) for each acquisition color of the imager 104. Nozzle bank 102 includes an array of nozzles, which includes a plurality of nozzle lines each nozzle line includes a plurality of nozzles. Each of at least one nozzle line is associated with a respective color to be printed. In other words each color is printed by a respective nozzle line or lines. A Nozzle line or lines which print a respective color is also referred to herein as a 'color unit'.

When one or more of the nozzles, such as nozzles 114 and 116, are malfunctioning, respective artifacts, such as streaks 118 and 120, may appear on the printed design and consequently in an image of the printed design acquired by imager 104. A streak may be a 'negative streak' (i.e., when a nozzle deposits less ink than intended) or a 'positive streak' (i.e., when a nozzle deposits more ink than intended) or a 'color streak' (i.e., a streak of the wrong color). Identifying the malfunctioning nozzles (also referred to as defective nozzles) as well as the type of malfunction (i.e., classifying the malfunction) is important to ensure the quality of the printed product. However, in general, the number of pixels sensors in sensor 108 may be smaller than the number of nozzles in each nozzle line (i.e., the resolution of the imager is smaller than then resolution of the digital printing press 100). Thus, more than one nozzle is associated with each pixel. Even when the number of pixels of imager 104 is equal or larger than resolution of printing press 100, the nozzles do not necessarily coincide with the pixels sensor in sensor 108 both in terms of alignment (i.e., a nozzle may print a respective dot in an area on the substrate, a portion of which is covered by one pixel sensor and the other portion of which is covered by an adjacent pixel sensor) and in terms of dot width (i.e., the dot width may be larger than the width covered by one pixel sensor)

Figure 2:
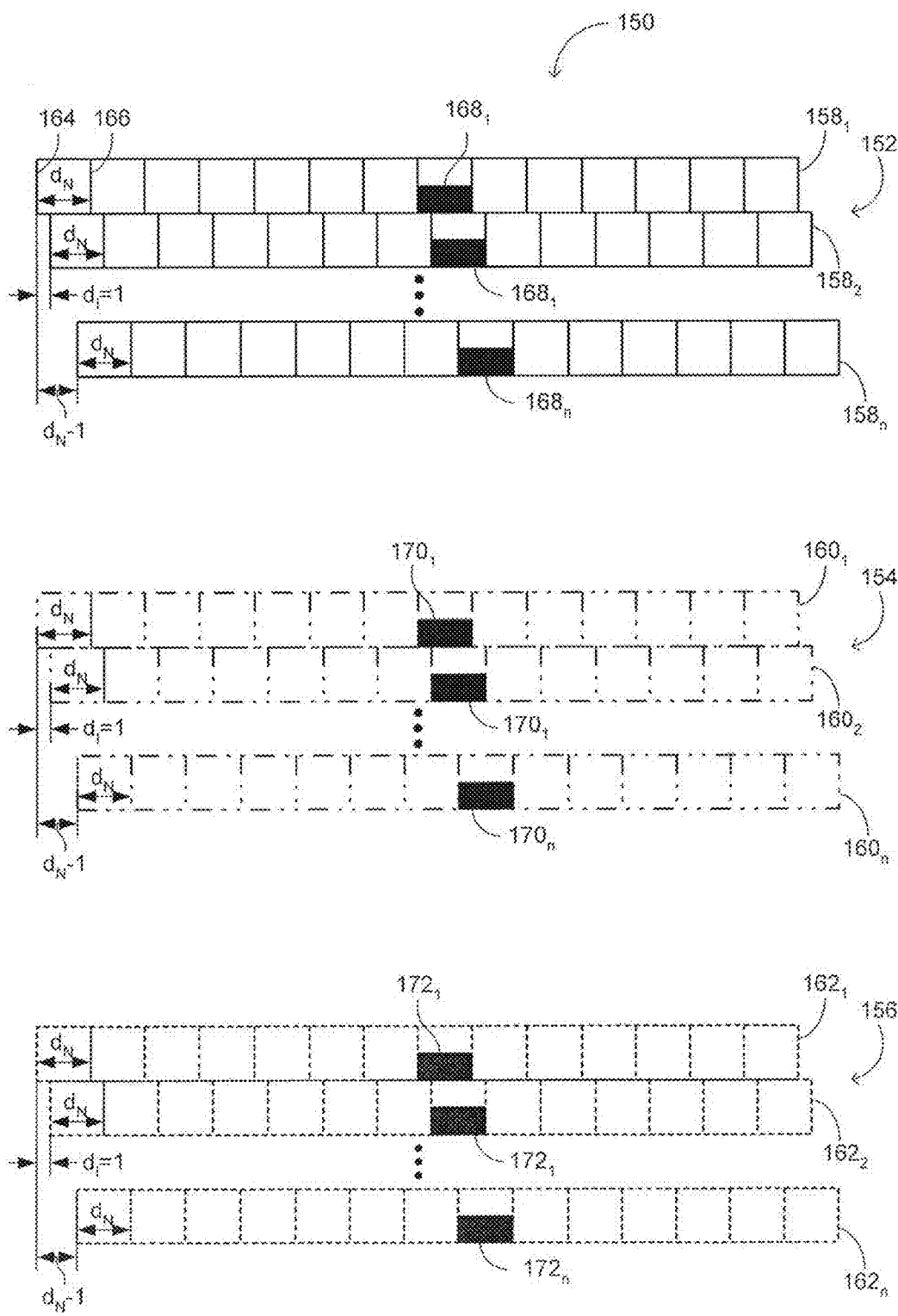
FIG. 2 is a schematic illustration of a nozzle pattern for detecting malfunctioning nozzles in a digital printing press, in accordance with another embodiment of the disclosed technique.

According to an embodiment of the disclosed technique, identifying the malfunctioning nozzle as well classifying the malfunction is achieved by printing a nozzle pattern and analyzing the acquired image of that pattern. Reference is now made to FIG. 2, which is a schematic illustration of a nozzle pattern, generally reference 150, for detecting malfunctioning nozzles in a digital printing press, in accordance with another embodiment of the disclosed technique. Nozzle pattern 150 includes a respective nozzle color pattern for each color being printed. In the example brought forth in FIG. 2, nozzle pattern 150 includes three nozzle color patterns 152, 154 and 156, also referred to as 'blocks', each respective of a color being printed. Each one of nozzle color patterns 152, 154 and 156 is associated with a respective block of nozzles (i.e., a line or lines of nozzles printing the same color). Each one of nozzle color patterns 152, 154 and 156 includes respective nozzle pattern rows printed across the substrate (i.e., perpendicular to the direction of motion of the substrate). Nozzle color pattern 152 includes nozzle pattern rows $158_1, 158_2, \ldots, 158_n$. Nozzle color pattern 154 includes nozzle pattern rows $160_1, 160_2, \ldots, 160_n$ and Nozzle color pattern 156 includes nozzle pattern rows $162_1, 162_2, \ldots, 162_n$.

As mentioned above, the number of pixels in sensor 108 may be smaller than the number of nozzles in each nozzle line. In order to have a single nozzle mark associated with at least one pixel, each nozzle pattern row is associated with unique respective nozzles, printing respective nozzle marks (e.g., nozzle marks 164 and 166), such that each nozzle in each row is spaced apart by a determined number of nozzles. For example, the nozzle marks in nozzle pattern rows $158_1$ $158_2, \ldots, 158_n$ of nozzle color pattern 152 are spaced apart by four nozzles. In other words line $158_1$ is associated with nozzles 1, 5, 9, . . . , n–4 which print respective nozzle marks. Line $158_2$ is associated with nozzles 2, 6, 10, . . . , n–3 which print respective nozzle marks. Line $158_n$ is associated with nozzles 4, 8, 12, . . . , n which print respective nozzle marks. Similarly, the nozzle marks in nozzle pattern rows $160_1$ $160_2, \ldots, 160_n$ of nozzle color pattern 154 are spaced apart by four nozzles and the nozzle marks in nozzle pattern rows $162_1$ $162_2, \ldots, 162_n$ of nozzle color pattern 154 are spaced apart by four nozzles. It is noted that nozzle pattern 150 is brought herein as an example of a nozzle pattern.

In general, a nozzle pattern includes a nozzle color pattern for each printed color. Each nozzle color pattern includes a plurality of nozzle pattern rows. Each row represents a sampling of 1 in K nozzles represented by the vertical marks (i.e., K is the sampling period in units of nozzles) printed in the respective color. Each row is shifted by an offset of 1 nozzle. In other words, in each block, row i/K prints nozzles i, i+k, i+2 k etc. The nozzles in each color unit are interleaved by one nozzle over K rows resulting in a full coverage of the nozzles of the color unit. In the example brought forth herein in conjunction with FIG. 2, K=4. K is determined according to the resolution of imager 104, such that single nozzle marks can be discerned and segmented in an image acquired by imager 104 and maximal expected deviation (E.g. if a nozzle deviates such that it 'jumps over the hurdle' of its i±k adjacent segments, an ambiguity may ensue).

Further included in a nozzle pattern 150 are nozzle locators for associating between nozzle marks in the acquired image of nozzle pattern 150 and the nozzles which printed that nozzle mark. Each one of nozzle pattern rows $158_1, 158_2, \ldots, 158_n$ includes a respective nozzle locator $168_1, 168_2, \ldots, 168_n$. Similarly, each one of nozzle pattern rows $160_1, 160_2, \ldots, 160_n$ includes a respective nozzle locator $170_1, 170_2, \ldots, 170_n$ and each one of nozzle pattern rows $162_1, 162_2, \ldots, 162_n$ includes a respective nozzle locator $172_1, 172_2, \ldots, 172_n$. Each one of nozzle locators $168_1, 168_2, \ldots, 168_n, 170_1, 170_2, \ldots, 170_n, 172_1, 172_2, \ldots, 172_n$ is printed by a predetermined respective set of nozzles in the respective nozzle pattern row thereof and exhibit a respective shape. In the example brought forth in FIG. 2, all of nozzle locators $168_1, 168_2, \ldots, 168_n, 170_1, 170_2, \ldots, 170_n$ and $172_1, 172_2, \ldots, 172_n$ exhibit a rectangular shape. However, a nozzle locator according to the disclosed technique may exhibit any pre-defined shape (i.e., geometrical such as a triangle, a square, a circle or an ellipse or an arbitrary shape which bay be defined in an image space according to pixels associated therewith). In general, nozzle locators $168_1, 168_2, \ldots, 168_n, 170_1, 170_2, \ldots, 170_n$ and $172_1, 172_2, \ldots, 172_n$ as well as the nozzle marks are identifiable in an image acquired by an imager such as imager 104 (FIG. 1). Since nozzle locators $168_1, 168_2, \ldots, 168_n, 170_1, 170_2, \ldots, 170_n$ and $172_1, 172_2, \ldots, 172_n$ were printed by a predetermined respective set of nozzles and the spacing between the nozzle marks in is also known, a processor (e.g., processor 106—FIG. 1) can associated between each nozzle mark in an image and the nozzle which printed that nozzle mark as further explained below.

To identify a malfunctioning nozzle, imager 104 acquires an image of the nozzle pattern and provides this image to processor 106. Furthermore, memory 107 provides processor 106 with information relating to the number of nozzle color patterns (i.e., blocks) in the nozzle pattern, the number of nozzle pattern rows in each block, the nozzle sampling period K, the height of each nozzle mark, the resolution of digital press 100 (e.g., 1200 Dots Per Inch–Dpi), the 'x-deviation threshold' and the 'strength score threshold' (the latter two are further explained below).

Processor 106 analyzes the image of the nozzle pattern. For each row, processor 106 determines the number of the reference nozzle (e.g., the nozzle left of the nozzle locator), a list of the nozzles numbers associated with the nozzle marks detected and the index of each mark in the row. Processor 106 further determines the deviation of the nozzle mark from the expected location of the nozzle mark (e.g., in millimeters or in pixel units), a strength score (e.g., a score between 0 to 1) and optionally nozzle classification (e.g., intact, missing, deviated, inconsistent, redundant as further explained below).

Initially, processor 106 segments the acquired image into the different nozzle color patterns (i.e., blocks) for example, according to the location of the nozzle color pattern in the acquired image and optionally according to the color of the nozzle color pattern. Processor 106 further segments each block into rows and each row into nozzle marks and nozzle locators. The nozzle marks identified from the segmented image of the nozzle pattern are referred to herein as 'detected nozzle marks'. Detecting and classifying a malfunctioning nozzle or nozzles employing a nozzle pattern is explained with the example of a single nozzle pattern row. It is however noted that this explanation relates to each of the nozzle pattern lines in the nozzle pattern.

Figure 3C:
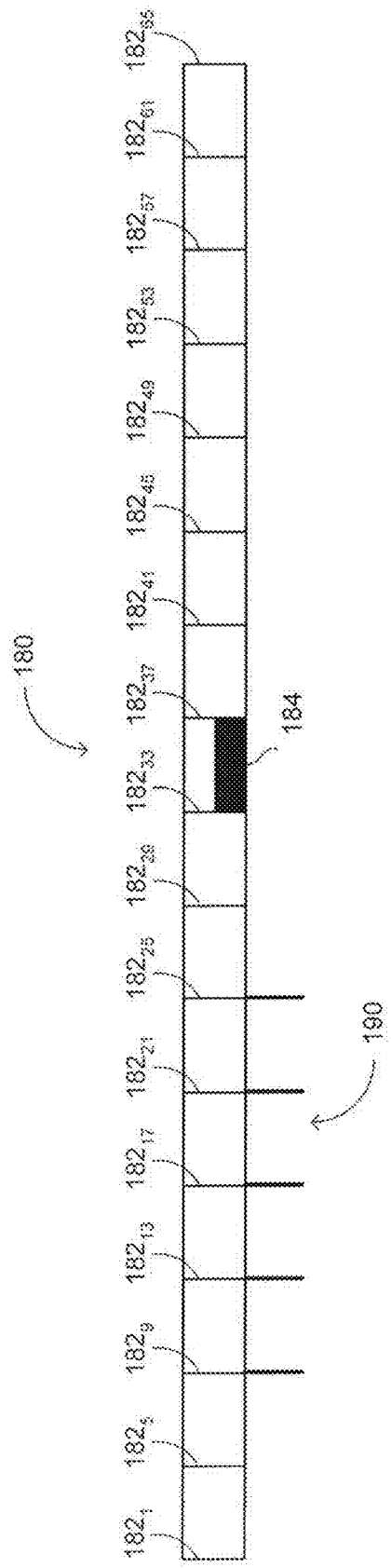

Reference is now made to FIGS. 3A, 3B and 3C, which are schematic illustrations of a single nozzle pattern row, generally referenced 180, in accordance with a further embodiment of the disclosed technique and referring also to FIG. 1. Nozzle pattern row 180 is similar to nozzle pattern rows $158_1, 158_2, \ldots, 158_n, 160_1, 160_2, \ldots, 160_n, 162_1, 162_2, \ldots, 162_n$ described hereinabove in conjunction with FIG. 2. Nozzle pattern row 180 includes 17 nozzle marks $182_1, 182_5, 182_9, 182_{13}, 182_{17}, 182_{21}, 182_{25}, 182_{29}, 182_{33}, 182_{37}, 182_{41}, 182_{45}, 182_{49}, 182_{53}, 182_{57}, 182_{61}$ and $182_{65}$ respective, for example, of each fourth nozzle in a line of nozzles (i.e., K=4) in a digital printing press, where the subscripts relate to the nozzle number printing the mark. Furthermore, nozzle pattern row 180 includes a nozzle locator 184 similar to nozzle locators $168_1, 168_2, \ldots, 168_n, 170_1, 170_2, \ldots, 170_n$ and $172_1, 172_2, \ldots, 172_n$ described hereinabove in conjunction with FIG. 2. Nozzle locator 184 is printed by nozzles number 33, 34, 35, 36 and 37, where the height of the marks printed by nozzles 34, 35 and 36 is a portion of the height of nozzle mark $182_{33}, 182_{37}$. In the example brought forth in FIGS. 3A, 3B and 3C, nozzle locator 184 exhibits the shape of a rectangle and is identifiable in an image acquired by imager 104 (FIG. 1).

To detect and classify a malfunctioning nozzle, initially processor 106 determines the center of gravity (i.e., the average location of the pixels in the segments) of each segment associated with a detected nozzle mark. Processor 106 employs this center of gravity as the location reference of the nozzle mark in the image. Furthermore, processor determines the 'strength score' of the nozzle mark, for example, by averaging the detected intensity level of each pixel in the segment associated with the nozzle mark. Also, processor 106 determines a local grid for a selected group of expected consecutive nozzle marks. The selected group of expected consecutive nozzle marks is also referred to herein as 'the grid window'. For example, in FIG. 3A, processor 106 determines a local grid for nozzle marks $182_5, 182_9, 182_{13}, 182_{17}$ and $182_{21}$ such that each one of nozzle marks $182_5, 182_9, 182_{13}, 182_{17}$ and $182_{21}$ is associated with a respective location in the local grid. To determine the local grid, processor 106 determines the spacing (i.e., the relative location) between consecutive detected nozzle marks in the selected group of nozzle marks. Thereafter, processor 106 determines the grid spacing (i.e., the distance between the grid points) that best fits the spacing between the nozzle marks, for example, according to the least square criterion. According to the least square criterion, the spacing between grid points is determined such that the sum of squared differences between the grid points and the nozzle marks are minimized. The start of the grid is anchored, for example, at a determined distance before the first nozzle mark in the group (e.g., at half the expected distance between the first nozzle mark in the group and the preceding nozzle mark). In other words, processor 106 determines the coefficients of the equations:

$$y = ax + b \qquad (1)$$

where a is the grid spacing and b is the anchor point before the first nozzle mark in the group. It is noted that the term 'distance' herein refers to the selected metric employed to determine the spacing, which can be measured, for example, in millimeters or pixel units. It is also noted that a special case of a local grid, such as described herein above, is the global grid, where the selected group of nozzle marks includes all of the detected nozzle marks in the row. It is further noted the total length (e.g., in millimeters or in pixel units) of the determined local grid may be different for each local grid since the determined grid spacing (i.e., a in equation (1)) is different. Also, the grid window is determined such that the probability that the nozzles printing in the grid windows malfunction, but that these nozzle marks shall appear to relate to intact nozzles (i.e., as further explained below), is below a determined threshold. It is noted that this threshold also relates to the aberrations in the imager optics (i.e., since such aberrations may cause a nozzle mark to appear in the image in a different location than the location in which the nozzle mark is actually located).

Once local grid 186 is determined, processor 106 employs local grid 186 to detect and classify malfunctioning nozzles. Processor 106 projects the determined local grid 186 on the image or the segment of the image which includes the selected group of expected consecutive nozzles. To determine a malfunctioning nozzle, processor 106 determines the expected location of each nozzle mark on local grid 186 (i.e., expected nozzle mark location), according to the resolution of digital press 100, the nozzle sampling rate K and the number of grid points. For example, and with reference to FIG. 3B, with a printing press resolution of 101.6 dpi, K=4 (i.e., which results in an expected spacing of 1 millimeter between nozzle marks) and 40 grid points, processor 106 determines that the expected nozzle mark location are spaced apart by 8 grid points. By anchoring the first grid point at half the expected distance between the first nozzle mark and the preceding nozzle mark, in FIG. 3B, processor 106 determines that grid locations $188_1$, $188_2$, $188_3$, $188_4$ and $188_5$ correspond to the expected nozzle mark locations. FIG. 3B exhibits an enlarged view of nozzle marks $182_1$, $182_5$, $182_9$, $182_{13}$, $182_{17}$, $182_{21}$ and $182_{25}$ and local grid 186 where nozzle marks $182_1$, $182_{17}$ are missing and nozzle mark $182_9$ has deviated. The expected location of nozzle marks $182_1$, $182_9$ and $182_{17}$ in nozzle pattern row 180 are marked with a dotted line. The grid locations corresponding to the expected location of nozzle marks $182_5$, $182_9$, $182_{13}$, $182_{17}$ and $182_{21}$ are depicted as thickened lines $188_1$, $188_2$, $188_3$, $188_4$ and $188_5$. An expected location of a nozzle mark, also referred to as 'grid slot'. As mentioned above, processor 106 projects the determined local grid 186 on the image or the segment of the image which includes the selected group of expected consecutive nozzles, for example, by determining the pixels corresponding to the grid slots in the image relative to the detected nozzle marks. Furthermore, processor 106 associates each detected nozzle mark (i.e., the location of the center of gravity of the segment with the nozzle mark) with a respective location on local grid 186 (i.e., the actual nozzle mark location). Furthermore, processor 106 associates each detected nozzle mark with the closest expected nozzle mark location thereto and determines the distance, $d_x$, therebetween.

A nozzle may be classified as 'intact' when a nozzle mark is identified in an expected nozzle mark location (i.e., within a determined tolerance). A nozzle may be classified as 'missing' if an expected nozzle mark location is not associated with a detected nozzle mark. A nozzle may be classified as 'deviated' if the distance, $d_x$, between the actual nozzle mark location and the expected nozzle mark location associated with the detected nozzle mark is above a threshold distance referred to herein also as the 'x-deviation threshold'. A nozzle may be classified as an 'inconsistent nozzle' (i.e., in terms of dot size and position consistency relative to previous dots) if the respective detected nozzle mark thereof exhibits a strength score above or below a determined 'strength score threshold'. The strength score threshold may be determined according to the statistics of the strength scores of the selected group of consecutive nozzle marks (e.g., below the average of the strength scores, or below the average minus the standard deviation of the strength scores and the like). A nozzle is classified as a 'redundant nozzle' when a nozzle mark is detected between two expected nozzle mark locations with detected nozzle marks associated therewith.

In general, a nozzle mark may be included in more than one selected group of nozzle marks (i.e., at least two groups of selected nozzle marks at least partially overlap). For example, the groups of nozzle marks are selected according to a sliding window over the detected nozzle marks starting from the first detected nozzle mark at a selected side of the row, where the sliding windows move toward the other side of the row. The step size of sliding window (i.e., the number of nozzles marks between the start of each window) such that each nozzle mark is included in at least one local grid and preferably in two or more local grids. When a nozzle mark is included in more than one group of selected nozzle marks, the detected information relating thereto (e.g., the difference between the expected and detected location) may be averaged, thus reducing the probability of miss detection and of determining erroneous information. For example, with reference to FIG. 3C, a local grid 190 is fitted to selected nozzle marks $182_9$, $182_{13}$, $182_{17}$, $182_{21}$ and $182_{25}$. Accordingly, nozzle marks $182_9$, $182_{13}$, $182_{17}$ and $182_{21}$ are included the selected group of nozzle marks to which both local grid 186 and local 188 were fitted. Thus, for example, the detected deviation of nozzle mark $182_9$, may be averaged. It is also noted that employing a local grid fitted to the spacing between a selected group of consecutive detected nozzle marks, reduces the effects on the acquired image of optical aberrations (e.g., local lens barrel/pincushion distortions) or motion of the printed substrate (e.g., a sheet or a continuous web) or both.

In some situation, the first or the first consecutive (e.g., the first two, the first three etc.) nozzle marks may be missing. In such a case, when a sliding window is employed, the first missing nozzles may not be detected since processor 106 does not detect a nozzle mark corresponding thereto. To identify such missing nozzles, processor 106 employs the results of the above mentioned segmentation and identifies nozzle locator 184. Also, as mentioned above, memory 107 provides processor 106 is with information relating to which nozzles printed nozzle locator 184. Accordingly, processor 106 can associate nozzle mark $182_{29}$ with nozzle 29 or mark $182_{33}$ with nozzle 33 or both. Thus, either nozzle mark $182_{29}$ or nozzle mark $182_{33}$ or both can be employed as reference nozzle marks. The information relating to the number of nozzles in each row (i.e., the expected number of nozzle marks) and the location of nozzles that printed nozzle locator 184 as well as nozzle marks mark $182_{29}$ or $182_{33}$ are available to processor 106. Processor 106 can determine the number of nozzle marks detected to the left and right of the reference nozzle mark. The difference between the number of detected nozzle (i.e., including the missing nozzles) and the expected number of nozzles is the number of first consecutive missing nozzles. It is noted that printing a nozzle locator, such as nozzle locator 184, with a plurality of consecutive nozzles, enables processor 106 to identify nozzle locator 184 even in the event of some of these nozzles are missing, since the size and shape of nozzle locator 184 are known. For example, processor 106 identifies a segment in the acquired image which matches a locator pattern template according to an image similarity measure (e.g., normalized cross correlation) between the template and the segment.

Also, the location of nozzles that printed nozzle locator 184 as well as the location of the reference nozzle marks are available to processor 106. Thus, processor 106 can identify each of the nozzles (e.g., determine the index or the bus address of the nozzles) in each nozzle pattern row according to the location of the reference nozzle marks and K. In other words, nozzle locator serves as a registration mark between the printed nozzle marks and the nozzles which printed those marks. Since nozzle marks may be identified as missing, the location of the missing nozzles can also be determined.

Figure 4:
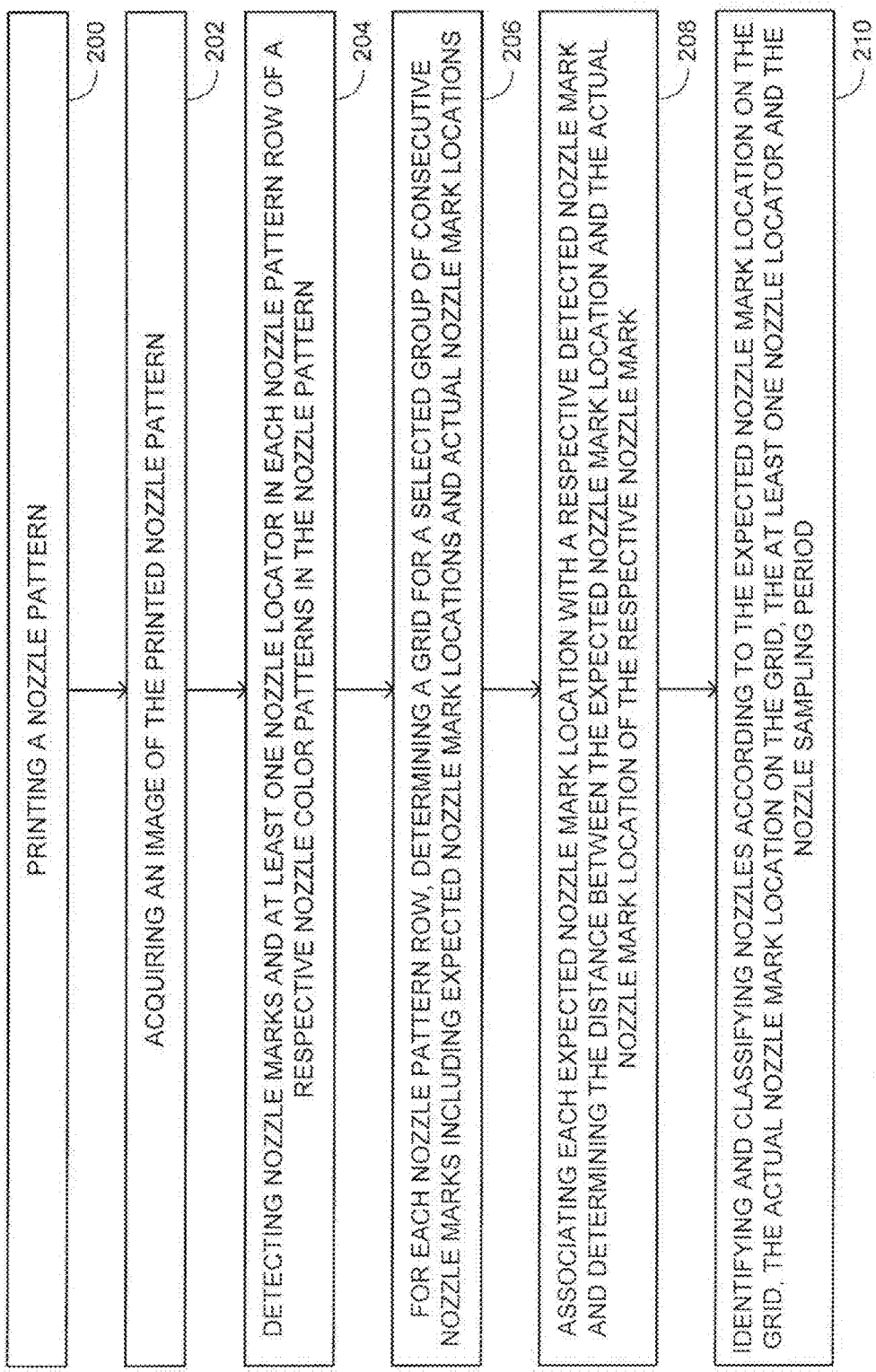
FIG. 4 is a schematic illustration of a method of identifying malfunctioning nozzles in a digital printing press.

Reference is now made to FIG. 4, which is a schematic illustration of a method of identifying malfunctioning nozzles in a digital printing press. In Procedure 200, a nozzle pattern is printed on a web or on a sheet. The nozzle pattern includes a respective nozzle color pattern for each color being printed. Each one of the nozzle color patterns is associated with a respective block of nozzles (i.e., a line or lines of nozzles printing the same color). Each nozzle pattern row is associated with unique respective nozzles, printing respective nozzle marks, such that each nozzle in each line is spaced apart by a determined number of nozzles. With reference to FIGS. 1 and 2, digital printing press 100 prints a nozzle pattern such as nozzle pattern 150.

In procedure 202, an image of the printed nozzle pattern is acquired. With reference to FIGS. 1 and 2, imager 104 acquires an image of nozzle pattern 150.

In procedure 204, nozzle marks and at least one nozzle locator are detected in each nozzle pattern row of a respective nozzle color patterns in the nozzle pattern. To identify the nozzle marks and the nozzle locator or locators, the acquired image is segmented into the different nozzle color patterns. The nozzle color patterns are further segmented into respective nozzle pattern rows and each nozzle pattern line is further segmented into respective nozzle marks and nozzle locators. With reference to FIGS. 1 and 2, processor 106 identifies nozzle marks such as nozzle marks 114 and 114 in nozzle pattern row $158_1$ of nozzle color pattern 152 in nozzle pattern 150.

In procedure 206, a grid is determined for a selected group of consecutive nozzle marks including expected nozzle mark locations and the actual nozzle mark location. The grid is determined, for example, by determining the grid spacing and anchor point which best fit the spacing between the selected group of consecutive nozzle marks as described above in conjunction with FIGS. 3A-3C. The actual nozzle mark location and the expected locations of nozzle marks on the grid are also determined also as described above in conjunction with FIGS. 3A-3C. The distance between With reference to FIG. 1, 3B, processor 106 determines a grid, such as local grid 186, for consecutive nozzle marks $182_5$, $182_9$, $182_{13}$ and $182_{21}$ where nozzle mark $182_{17}$ is missing. Thickened lines $188_1$, $188_2$, $188_3$, $188_4$ and $188_5$ represent the expected location of nozzle marks $182_5$, $182_9$, $182_{13}$, $182_{17}$ and $182_{21}$ In procedure 208, each expected nozzle mark location is associated with a respective detected nozzle mark and the distance, $d_x$, between the expected nozzle mark location and the actual nozzle mark location (i.e., of the respective nozzle mark) is determined as described above in conjunction with FIGS. 3A-3C. As described above each nozzle mark (i.e., the location of the center of gravity of the segment associated with the nozzle mark) is associated with a respective location on the local grid. Furthermore, each nozzle mark is associated with the closest expected nozzle mark location thereto and the distance, $d_x$, between the actual nozzle mark location and the expected nozzle mark location is determined. With reference to FIG. 1, processor 106 associates each expected nozzle mark location with a respective nozzle mark and determines the distance between the expected nozzle mark location and the actual nozzle mark location.

In procedure 210, nozzles are identified and classified according to the expected nozzle mark location on the grid, the actual nozzle mark location on the grid, the nozzle locator and the nozzle sampling period K. A nozzle may be classified as 'intact' when a nozzle mark is identified in an expected location of a nozzle mark location (i.e., within a determined tolerance). A nozzle may be classified as 'missing' when an expected nozzle mark location is not associated with a detected nozzle mark. A nozzle may be classified as 'deviated' when the distance, $d_x$, between the actual nozzle mark location and the expected nozzle mark location associated with the detected nozzle mark is above the x-deviation threshold. A nozzle may be classified as an 'inconsistent nozzle' when the respective nozzle mark thereof exhibits respective strength score below the strength score threshold. A nozzle may be classified as a 'redundant nozzle' when a nozzle mark is detected between two expected nozzle mark locations with nozzle marks associated therewith. Furthermore, the first or the first consecutive missing nozzles are identified by identifying a reference nozzle mark in the nozzle locator. Since the number of nozzles printing in each row is known and the number of nozzle marks to the left and right of the reference nozzle mark are also determined, the difference between the number of detected nozzle (i.e., including the missing nozzles) and the expected number of nozzles is the number of first consecutive missing nozzles. Also, the location of nozzles that printed the nozzle locator, as well the location of the reference nozzle marks are known. Thus, each of the nozzles in each nozzle pattern row can be identified (e.g., determine the index or the bus address of the nozzles) according to the location of the reference nozzle marks (as determined from the nozzle locator) and K. Since nozzle marks may be identified as missing, the location of the missing nozzles can also be determined. With reference to FIG. 1, processor 106 identifies and classifies malfunctioning nozzles.

The nozzle pattern described above in conjunction with FIGS. 2, 3A-3C and 4 enables detecting a missing nozzle, a deviated nozzle, an inconsistent nozzle and a redundant nozzle. However, each nozzle may deposit a different amount of ink for a given dot size (e.g., the dot diameter), resulting in inconsistency in the dot size printed on the substrate. The dot size printed on the substrate is also referred to herein as 'coverage', 'ink density' or just 'density'. Inconsistency in the dot size may result from different electrical characteristics (e.g., different resistances, capacitance and the like) of the mechanism, also referred to as 'nozzle head', of the nozzle printing the dot.

Figure 5:
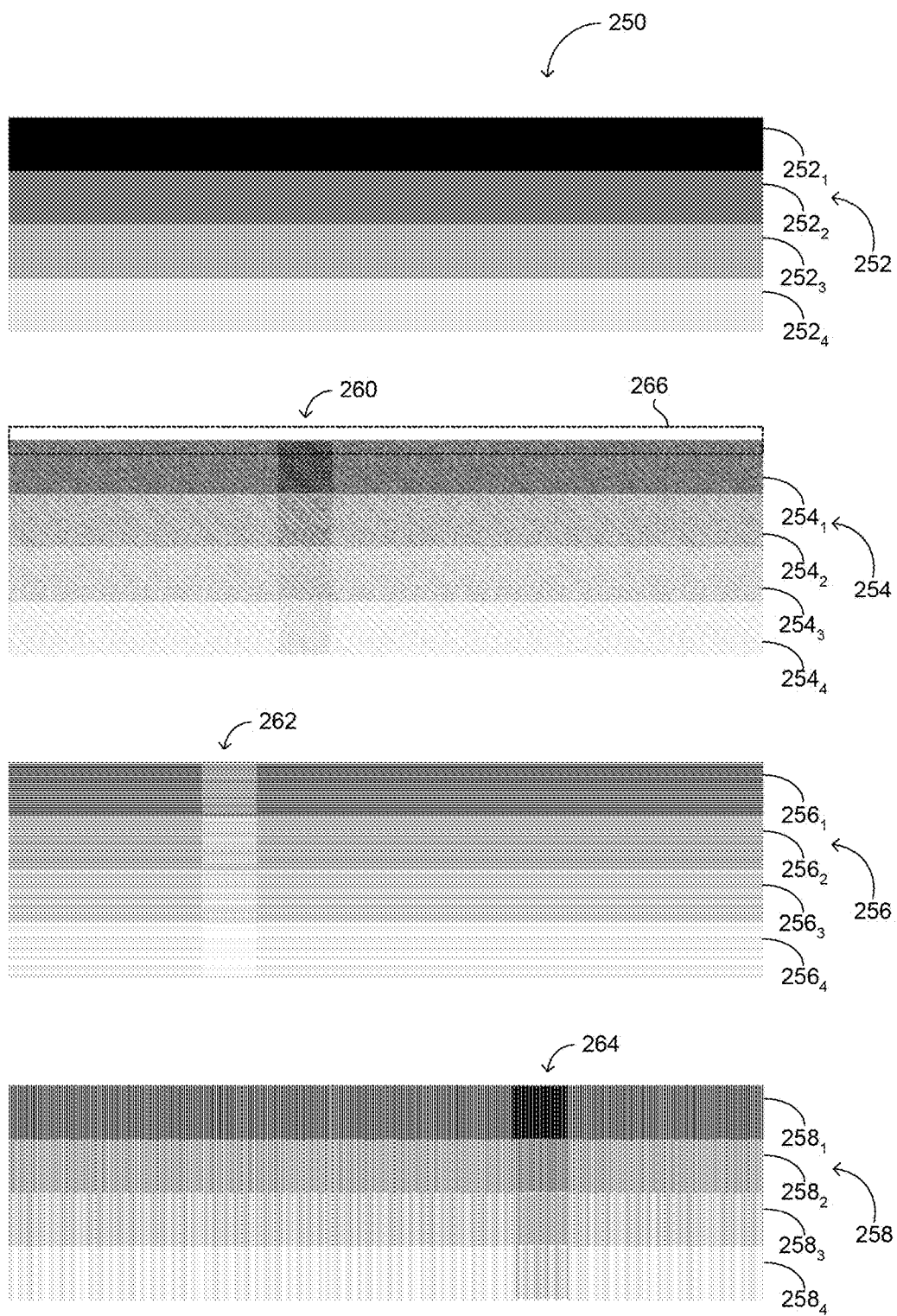
FIG. 5 is a schematic illustration of a uniformity pattern constructed and operative in accordance with a further embodiment of the disclosed technique.

Such inconsistency in the dot size printed on the substrate may result in different shades of color being printed rather than a uniform shade of color. This phenomenon is also known as 'banding' and may affect the printed quality of the design. Accordingly, it would be beneficial to determine which nozzles or group of nozzles deposit a different amount of ink for a given dot size. To that end a uniformity pattern is printed on the substrate. It is noted that the uniformity pattern is different from the nozzle pattern described above. Reference is now made to FIG. 5, which is a schematic illustration of a uniformity pattern generally referenced 250, constructed and operative in accordance with a further embodiment of the disclosed technique. Uniformity pattern 250 includes a plurality of color uniformity patterns respective of each color being printed. In the example brought forth in FIG. 5, uniformity pattern 250 includes four color uniformity patterns, color uniformity pattern 252 respective of the color black, color uniformity pattern 254 respective of the color magenta, color uniformity pattern 256 respective of the color cyan, color uniformity pattern 258 respective of the color yellow. Each one of color uniformity pattern, 252, 254, 256 and 258 includes a plurality of color uniformity rows printed across the substrate. Each color uniformity row in each color uniformity pattern is associated with a respective different planned ink density level (i.e., the density intended to be printed). Furthermore, respective color uniformity rows in each color uniformity patterns may be associated with the same ink density levels different form the ink density levels of other respective rows. In the example brought forth in FIG. 5, each one of color uniformity pattern, 252, 254, 256 and 258 includes four color uniformity rows respective of the same four different ink density levels. Color uniformity pattern 252 includes color uniformity row $252_1$ associated with very high planned density (e.g., a value between 85% to 100% of the largest possible dot size on the substrate), color uniformity row $252_2$ associated with high planned density (e.g., a value between 60% to 75% of the largest possible dot size on the substrate), color uniformity row $252_3$ associated with medium planned density (e.g., a value between 35% to 50% of the largest possible dot size on the substrate) and color uniformity row $252_4$ associated with low planned density (e.g., a value between 10% to 25% of the largest possible dot size on the substrate). Similarly, color uniformity pattern 254 includes color uniformity row $254_1$, $254_2$, $254_3$ and $254_4$ associated with very high, high, medium and low densities respectively, color uniformity pattern 256 includes color uniformity row $256_1$, $256_2$, $256_3$ and $256_4$ also associated with very high, high, medium and low densities respectively, color uniformity pattern 254 includes color uniformity row $258_1$, $258_2$, $258_3$ and $258_4$ which are also associated with very high, high, medium and low densities respectively. It is noted that the planned density level printed by each color uniformity row may be determined, for example, according to the parameters of the printing press such as dot gain resolution, dpi and the like. It is further noted, all of the nozzle associated with the respective color are employed in printing color uniformity rows $252_1$-$252_4$, $254_1$-$254_4$, $256_1$-$256_4$ and $258_1$-$258_4$.

As mentioned above, each nozzle may deposit a different amount of ink for a given dot size, resulting in inconsistency in the dot size printed on the substrate. In FIG. 5, the nozzles printing the color black all print the same dot size. As such color uniformity pattern 252 exhibits a uniform shade for color uniformity rows $252_1$, $252_2$, $252_3$ and $252_4$. With regards to the color magenta, a portion of the nozzles printing the color magenta print a larger dot size. As such, a section 260 in each color uniformity rows $254_1$, $254_2$, $254_3$ and $254_4$ exhibit a darker shade. With regards to the color cyan, a portion of the nozzles printing the color cyan print a smaller dot size. As such, a section 262 in each color uniformity rows $256_1$, $256_2$, $256_3$ and $256_4$ exhibit a lighter shade. With regards to the color yellow, a portion of the nozzles printing the color yellow print a larger dot size. As such, a section 264 in each color uniformity rows $258_1$, $258_2$, $258_3$ and $258_4$ exhibit a darker shade.

To determine which nozzles prints a different dot size and referring also to FIG. 1, digital printer 100 prints a uniformity pattern such as uniformity pattern 250. Imager 104 acquires an image of the printed uniformity pattern and provides the acquired image to processor 106. Processor 106 is provided with information relating to the number of colors being printed, the number of rows in each color uniformity pattern, the height of each row, the resolution of the digital press, the resolution of the imager, and the spacing between each the rows in each color uniformity pattern and the spacing between the color uniformity patterns. Processor 106 provides a map (e.g., a two dimensional Look Up Table) of the relative intensities of the rows as further explained below.

Processor 106 segments the acquired image into color uniformity patterns. Processor 106 further segments each color uniformity pattern into color uniformity rows. Processor 106 determines the relative density of each bin (i.e., pixel or group of pixels depending on the resolution of the imager relative to the resolution of the digital printing press) across each color uniformity row. The relative density is determined according to the following:

$$d=[i_x]=\log I[i_x]/I_o$$

where $i_x$ relates to the bin number, $I[i_x]$ relate to the detected intensity of the row (i.e., as detected by imager 104), where the subscript x represents the fact that the measurements are made across the substrate and $I_o$ relates to the detected intensity of the substrate (i.e., also as detected by imager 104). By determining the relative densities across the bins in one of color uniformity rows $258_1$, $258_2$, $258_3$ and $258_4$ of the uniformity pattern 250, processor 106 determines a color uniformity map where each bin at each row is associated with a respective relative density. The map may be in the form of a two dimensional LUT where the rows correspond to the color uniformity rows and the columns corresponds to the bins. Processor 106 can determine the compensation required at each bin to achieve uniform color density according to the difference or the ration between the planned density (i.e., the density intended to be printed) and detected density in each bin. Since, in general, all the nozzles print the uniformity pattern, each of the bins is associated with a respective nozzle or group of nozzles. Thus when the bin associating non-uniformity is identified, the nozzles printing that non-uniform bin are also identified.

Figure 6:
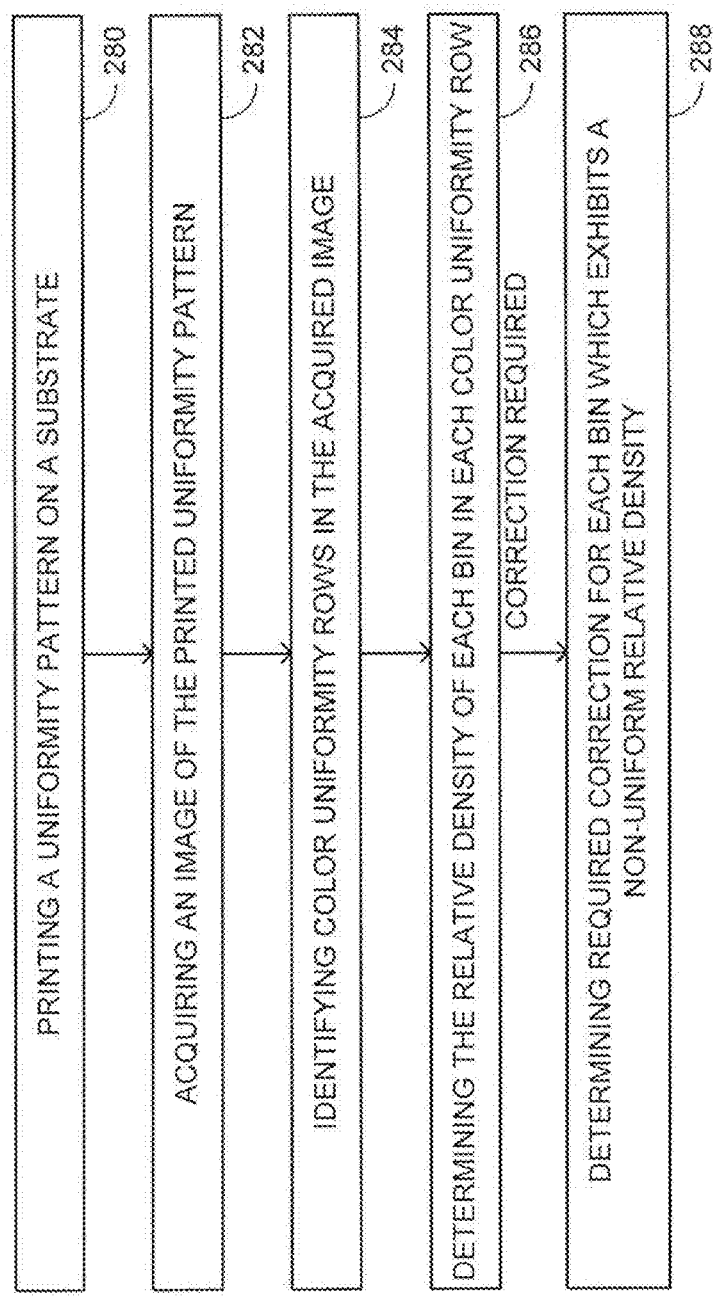
FIG. 6 is a schematic illustration of a method for determining inconsistency in ink density in a digital printing press, operative in accordance with another embodiment of the disclosed technique.

Reference is now made to FIG. 6, which is a schematic illustration of a method for determining inconsistency in ink density in a digital printing press, operative in accordance with another embodiment of the disclosed technique. In procedure 280, a color uniformity pattern is printed on a substrate. The Uniformity pattern includes a plurality of color uniformity patterns respective of each color being printed. Each color uniformity pattern includes a plurality of color uniformity rows printed across the substrate. Each color uniformity row is associated with a respective of a different planned ink density level. With reference to FIGS. 1 and 5, digital printing press 100 (FIG. 1) prints uniformity pattern 250 (FIG. 5).

In procedure 282, an image of the printed color uniformity pattern is acquired. With reference to FIGS. 1 and 5, imager 104 (FIG. 1) acquires an image of uniformity pattern 250 (FIG. 5).

In procedure 284, color uniformity rows are identified in the acquired image. The color uniformity rows are identified by segmenting the acquired image of the uniformity pattern. With reference to FIGS. 1 and 5, processor 106 identifies color uniformity rows $252_1$-$252_4$, $254_1$-$254_4$, $256_1$-$256_4$ and $258_1$-$258_4$.

In procedure 286, the relative density of each bin in each color uniformity row is determined. Each bin relates to a pixel or a group of pixels in the image depending on the resolution of the imager relative to the resolution of the digital printing press. With reference to FIGS. 1 and 5, processor 106 determines the relative density in each bin in each of color uniformity rows $252_1$-$252_4$, $254_1$-$254_4$, $256_1$-$256_4$ and $258_1$-$258_4$.

In procedure 288, a required correction for each bin is determined, which exhibits a non-uniform relative density.

The required correction is determined such that uniform density is achieved for at each row according to the difference or the ration between the planned density and detected density in each bin. With reference to FIG. 1, processor 106 determines the correction required at each bin to achieve uniform color density according to the difference or the ration between the planned density and detected density in each bin.

The above described uniformity pattern may also be employed for identifying the presence of a missing nozzle, a deviated nozzle, an inconsistent nozzle or a redundant nozzle. As mentioned above, when at least one of the nozzles is either missing, deviated inconsistent or redundant, a streak may appear on the printed substrate and consequently in the acquired image. Accordingly, referring to FIG. 1, processor 106 identifies such a streak in an acquired image of the uniformity pattern. When processor 106 identifies such a streak in the image (e.g., by identifying regions of reduced density in the density uniformity pattern or identifying segments in the image exhibiting elongated shape), the processor 106 determines the group of nozzles from which the streak originated (i.e., the suspected nozzles) according to the location of the streak in the image. Processor 106 can then instruct digital press 100 to print a nozzle pattern for only a portion of the nozzles which includes the suspected nozzles (i.e., the number of nozzles in the portion printing the nozzle pattern may be larger than the number of suspected nozzles). Thus, the processing time required to identify the nozzle causing the streak as well as substrate waste may be reduced.

When employing a nozzle pattern or a uniformity pattern such as described above, the acquired images of these patterns are converted to gray level imagers (i.e., for reducing the required processing thereof). One alternative for converting a color image such as a RGB image into a grey scale image is averaging the intensities of the Red Green and Blue channels. However, since the appearance of color in an image is also affected by the background, simply averaging the intensities may lead to a gray level image which does reflect the relative intensities of the color image (e.g., when printing yellow, the average or RGB intensity values may render the intensity of yellow as low relative to the intensity of the background). Furthermore, when associating a specific principle channel (e.g., Red Green or Blue) of a selected color (e.g. we analyze the 'Cyan' uniformity pattern over the 'red' channel of the imager), for colors such as orange, green, violet or spot colors such as Pantone colors, the intensity values from more than one acquisition channel may be needed to determine the relative intensity of the color. To avoid such occurrences, according to the disclosed technique, and with reference to FIGS. 5 and 1, for each color, processor 106 selects from the color uniformity row with the maximum coverage, an area in the image, such as area 266, which includes substantially the same number of color pixels and background pixels. Processor 206 determines the standard deviation of the intensity levels of the pixels for that color according to the intensities of the pixels in the selected area. Processor 106 than weighs each of the determined standard deviations of each color (e.g., by dividing the determined standard deviation of the intensities of each color by the sum of determined standard deviations), and determines the weighted average of the RGB intensities at each channel, for each color, to determine the grey level for that color.

Figure 7:
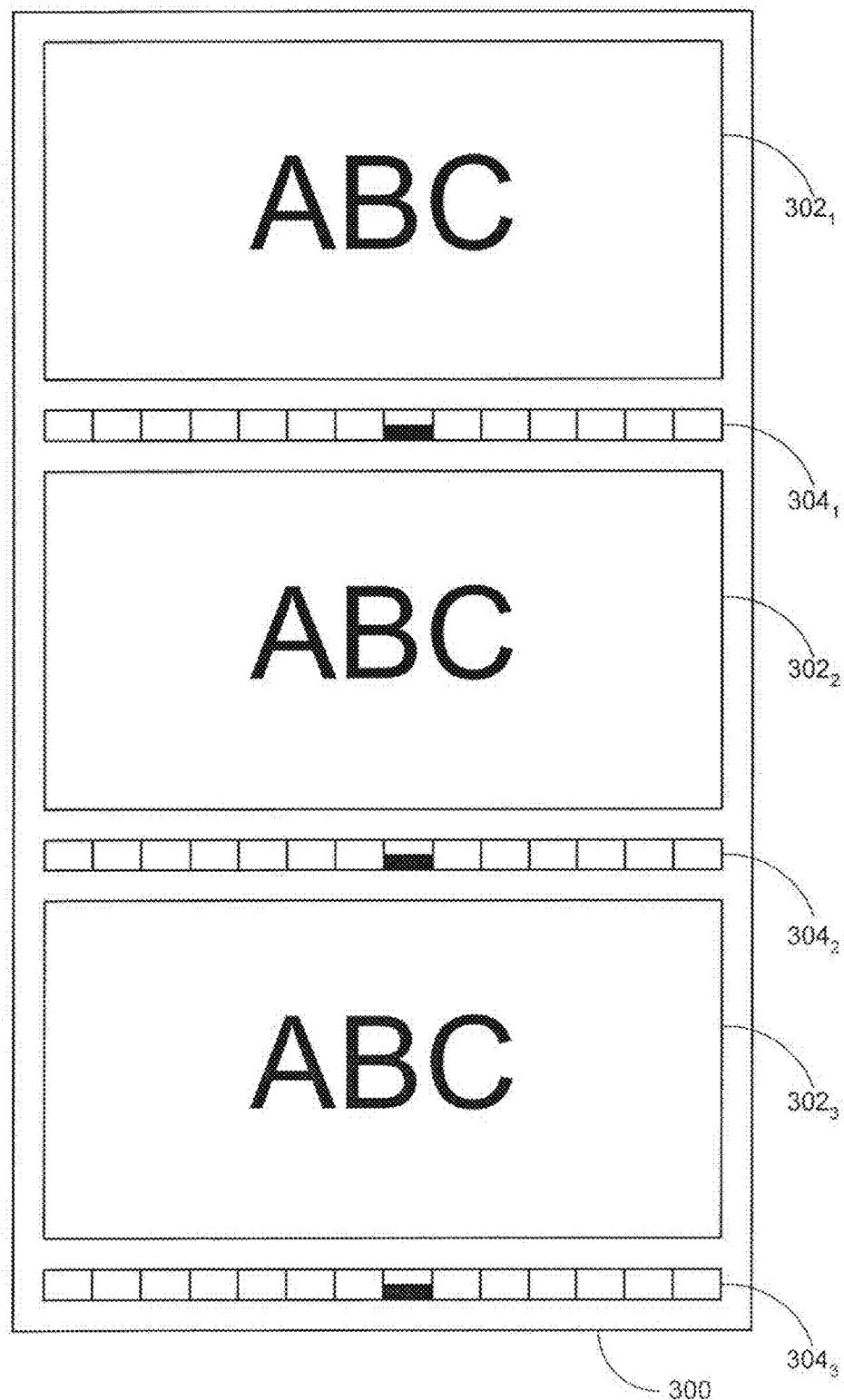
FIG. 7 is a schematic illustration of a substrate on which a printed design, as well as portions of a pattern are printed in the margins.

In some cases, it would not be possible to print an entire pattern such as the above described nozzle pattern or uniformity pattern. The partition of these patterns into rows, enables printing only portions of these patterns, for example, in the top or bottom margins of the printed design. These printed portions of the patterns may then be cut out from the final product to be delivered. For example, when the digital printing press prints labels, a portion of a pattern may be printed on the dye cut of the label. Reference is now made to FIG. 7, which is a schematic illustration of a substrate, generally referenced 300, on which a printed design as well as portions of a pattern (i.e., a nozzle pattern or a uniformity pattern) are printed in the margins. Depicted in FIG. 7 is a plurality of designs $302_1$, $302_2$ and $302_3$. Portions $304_1$, $304_2$ and $304_3$ of a pattern for detecting malfunctioning nozzles (i.e., a portion of the nozzle pattern or a portion of the uniformity pattern) are printed in the margins between designs $302_1$, $302_2$ and $302_3$. Although portions $304_1$, $304_2$ and $304_3$ are depicted in FIG. 7 as nozzle pattern rows, it is noted that portions $304_1$, $304_2$ and $304_3$ of a pattern may be a single row in a pattern (i.e., either a nozzle pattern rows or a color uniformity row) or a color pattern (i.e., either a nozzle color pattern or a color uniformity pattern). To acquire an image of the entire pattern, and with reference to FIG. 1, imager 104 acquires an image of each one of portions $304_1$, $304_2$ and $304_3$ and processor 106 and generates a composite image of the pattern.

Figure 8:
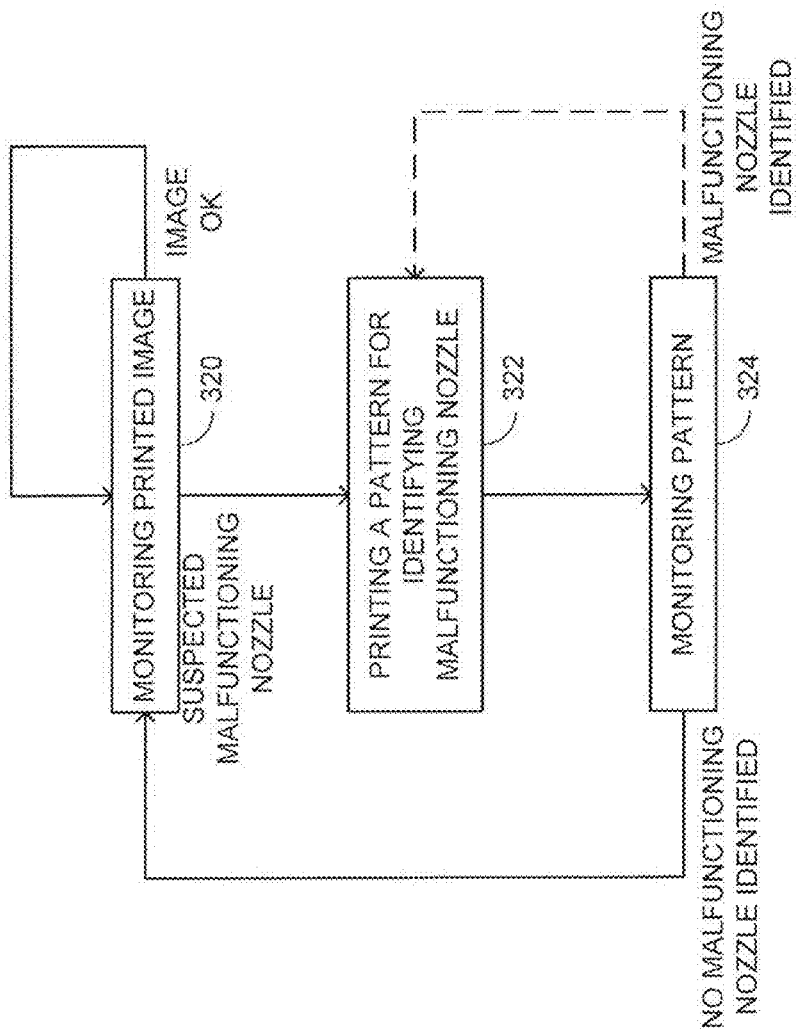
FIG. 8 is a schematic illustration of a state machine employed for detecting malfunctioning nozzles with either a nozzle pattern or a uniformity pattern or both, operative in accordance with a further embodiment of the disclosed technique.

Reference is now made to FIG. 8, which is a schematic illustration of a state machine employed for detecting malfunctioning nozzles with either a nozzle pattern or a uniformity pattern or both, operative in accordance with a further embodiment of the disclosed technique. In state 320, the printed image is monitored for streaks or banding or both. When the printed image is O.K. the state machine remains in state 320. If a suspected malfunctioning nozzle is identified in the image, the state machine proceeds to state 322. In state 322, one of a nozzle pattern or a uniformity pattern or both are printed and the state machine proceeds to state 324. In state 324 the printed pattern is monitored to identify, classify the malfunctioning nozzle. According to one alternative, the state machine always returns to state 320 after state 324. According to another alternative, the state machine returns to state 322 when the malfunctioning nozzle is identified (as indicated by the dashed line) to validate the compensation of the defective nozzle or nozzles, and returns to state 320 when the no malfunctioning nozzle is identified.

Figure 9:
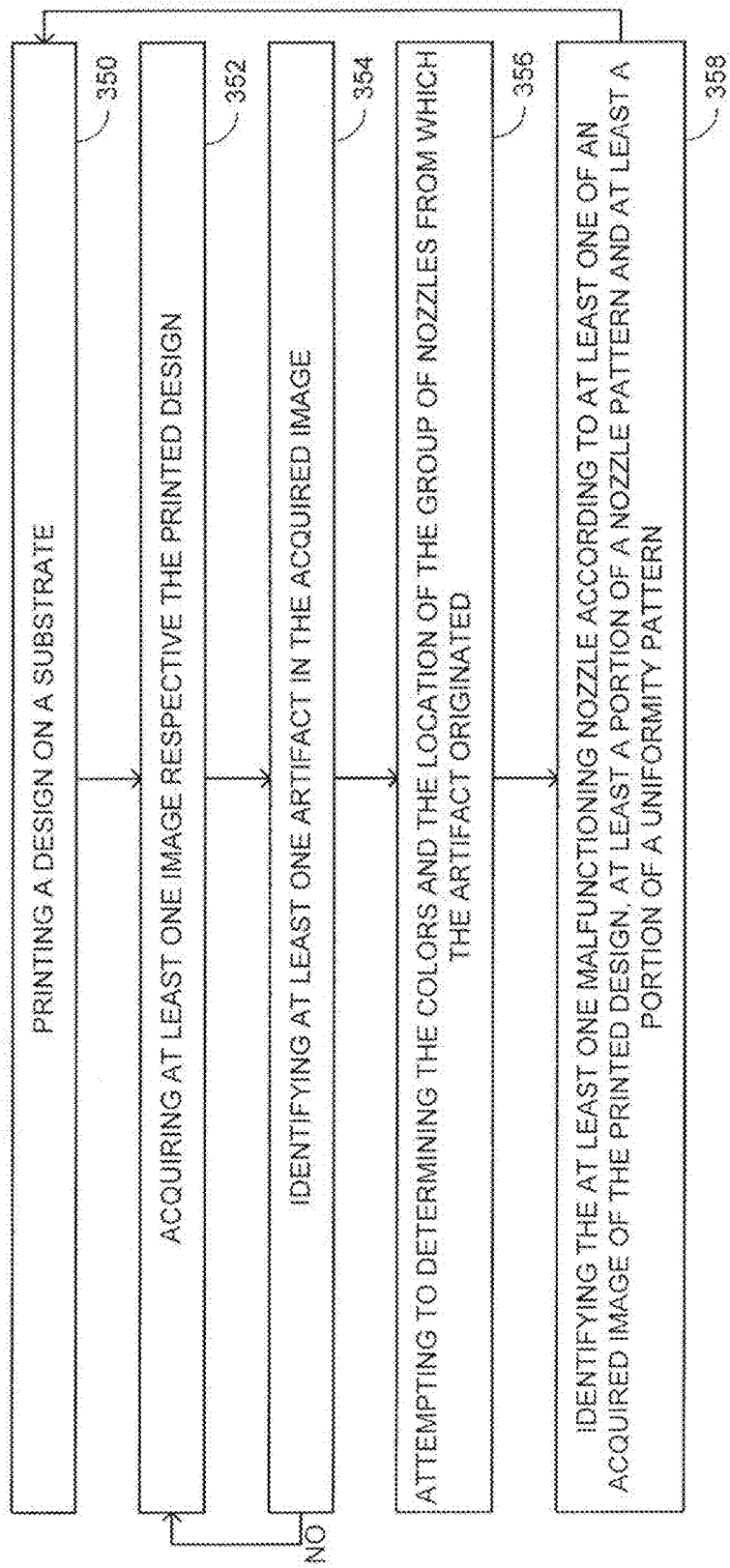
FIG. 9 is a schematic illustration of an exemplary method implementing the above described state machine.

Reference is now made to FIG. 9, which is a schematic illustration of an exemplary method implementing the above described state machine. In procedure 350, a design is printed on a substrate. With reference to FIG. 1, digital printing press 100 prints a design on a substrate.

In procedure 352 at least one image respective of the printed design is acquired. With reference to FIG. 1, imager 104 acquires at least one images of the printed design.

In procedure 354, at least one artifact is identified in the acquired images. The artifact may be a streak in the images or a band of non-uniform shade of color or both. Streaks may be identified by segmenting the images and detecting elongated segments (e.g., exhibiting a length to width ratio above a determined threshold). Banding may be identified by selecting in the reference image (e.g., Raster Image Processor-RIP images) areas of uniform color, and detecting in the images resulting from each acquisition channel differences in color uniformity in those regions. Alternatively, a difference image may be determined by subtracting the acquired images from a reference image (e.g., a PDF of the design, an image of the printed design determined as a reference). The difference images may also be segmented to determined steaks and banding as described above. With reference to FIG. 1, processor 106 identifies at least one artifact in the acquired images. When artifacts are identified, the method proceeds to procedure 356. When artifacts are not identified, the method returns to procedure 350.

In procedure 356, the colors and the location of the group of nozzles from which the artifact originated is attempted to be determined. The location of the group of malfunctioning nozzles from which the artifact originated may be determined by the location of the artifact on the X-axis of the image (i.e., the axis perpendicular to the direction of motion of the substrate). Since the resolution of the image may be smaller than the resolution of the printing press and since some of the nozzles at the ends of the nozzle bank may not be printing, the location of the malfunctioning nozzle causing the artifact can only be known to a certain degree of confidence. This degree of confidence defines the group of suspected malfunctioning nozzles. The color of the suspected malfunctioning nozzles may be determined by identifying the colors which the artifact exhibits, relative to the predicted color at the location of the artifact (e.g., from a reference image or from neighboring pixels). At the worst case, the group of nozzles determined as the group of nozzles from which the artifact originated includes nozzles from all the colors printed by the printing press. Furthermore, registration features (e.g., designated registration marks or features in the printed design) are determined to allow association between the regions in the image and the nozzles printing those regions. The printing press knows which nozzles printed which parts of the printed design and thus which nozzles printed the registration features. Identifying the location of the registration features in the image results in a correspondence (i.e., registration) between the printed image and the nozzles which printed the image. With reference to FIG. 1, processor 106 determines at least one of the color and the group of malfunctioning nozzles causing the at least one artifact. It is noted that procedure 356 is optional.

In procedure 358, the at least one malfunctioning nozzle is identified and the malfunction is optionally classified, according to at least one of an acquired image of the printed design, at least a portion of a nozzle pattern (e.g., nozzle pattern 150—FIG. 2) and at least a portion of a uniformity pattern (e.g., uniformity pattern 250—FIG. 5). The portion of the nozzle pattern or the uniformity pattern relates to at least one of the color and the group of malfunctioning nozzles causing the artifact or artifacts. Identifying and optionally classifying the malfunctioning nozzle according to at least a portion of a nozzle pattern and at least a portion of a uniformity pattern is performed as described above in conjunction with FIGS. 2, 3A-3C, 4, 5 and 6 respectively. Identifying the malfunctioning according to an acquired image or images of the printed design is further explained below. With reference to FIG. 1, processor 106 identifies the malfunctioning nozzle according to at least one of an acquired image of the printed design, at least a portion of a nozzle pattern and at least a portion of a uniformity pattern. After procedure 358, the method returns to procedure 350

As mentioned above malfunctioning nozzles may be identified from an acquired image of the printed design in which an artifact is identified. The image in which the artifact is identified is referred to herein as 'the first artifact image'. According to one alternative, each one of the suspected nozzles is turned off (e.g., by turning off the print heads of the digital printer). For each suspected nozzle that is turned off, another repetition of design is printed on the substrate and an image thereof is acquired. When a change (e.g., a new streak) occurs in the newly acquired image relative to the first artifact image, then the nozzle that was turned off is not the malfunctioning nozzle. When no change occurs in the newly acquired image relative to the first artifact image, then the nozzle that was turned off is determined to be a malfunctioning nozzle. According to another alternative, each one of the suspected nozzles is compensated for. For each compensated suspected nozzle, another repetition of design is printed on the substrate and an image thereof is acquired. When no artifacts appear in the newly acquired image relative to the first artifact image, then the malfunctioning nozzle has been identified and compensated for. At the worst case of both of the above described alternative. An exhaustive search is conducted to identify the malfunctioning nozzle or nozzles. It is also noted that verifying that nozzle compensation was successful may also be achieved when the printed design in the next cycle of the digital printing press is different from the printed design being inspected (i.e., assuming the new design does not include an intended streak at the same location and that the suspected nozzles print in the new design).

In some cases, the substrate employed for printing is non-opaque. In such case, when a pattern (e.g., a uniformity pattern or a nozzle pattern) is printed on the substrate the contrast between the pattern and the background may be low, rendering the pattern un-identifiable in the acquired image thereof. Also, in a hybrid printing press (e.g., a flexographic press followed by a digital press) the pattern may be printed on the colors printed by the flexographic, which may also render the pattern un-identifiable in the acquired image thereof. Since, in many digital printing press the first color unit prints the color white, according to the disclosed technique, when non-opaque substrates are employed or in hybrid printing presses, the pattern is printed over a layer of white ink (i.e., printed by the white color unit of the digital press) to enable analysis of the pattern.

It will be appreciated by persons skilled in the art that the disclosed technique is not limited to what has been particularly shown and described hereinabove. Rather the scope of the disclosed technique is defined only by the claims, which follow.

The invention claimed is:

1. A method of identifying at least one malfunctioning nozzle in a digital printing press, said digital printing press including a plurality of nozzles, the method comprising the procedures of:

printing a design on a substrate;
acquiring at least one image of the printed design;
identifying at least one artifact in the acquired image; and
identifying said malfunctioning nozzle and classifying a malfunction of said at least one malfunctioning nozzle according to said at least one of said acquired image of said printed design, at least a portion of a nozzle pattern, and at least a portion of a uniformity pattern, by:
printing at least said portion of said nozzle pattern, said nozzle pattern including a nozzle color pattern for each of at least one printed color, each nozzle color pattern including a plurality of nozzle pattern rows, each nozzle pattern row including a plurality of nozzle marks representing samples of 1 in K nozzles, each row shifted by an offset of 1 nozzle, each nozzle pattern row further including at least one nozzle locator;
acquiring an image of the printed portion of said nozzle pattern;
detecting nozzle marks and said at least one nozzle locator in each of said nozzle pattern rows of the respective nozzle color patterns in said portion of said nozzle pattern;

for each nozzle pattern row, determining a grid for a selected group, of consecutive nozzle marks including expected nozzle mark locations and actual nozzle mark locations;

associating each expected nozzle mark location with a respective detected nozzle mark and determining the distance between the expected nozzle mark location and the actual nozzle mark location of the respective nozzle mark; and identifying and classifying nozzles according to the expected nozzle mark location on said grid, the actual nozzle mark location on said grid, the at least one nozzle locator, and K, and wherein a nozzle is classified as intact when a nozzle mark is identified in an expected nozzle mark location within a determined tolerance, wherein a nozzle is classified as missing when an expected nozzle mark location is not associated with a detected nozzle mark, wherein a nozzle is classified as deviated when the distance between said actual nozzle mark location and said expected nozzle mark location associated with the detected nozzle mark is above an x-deviation threshold, wherein a nozzle is classified as inconsistent when the respective detected nozzle mark thereof exhibits a strength score below a determined strength score threshold, and wherein nozzle is classified as redundant when a nozzle mark is detected between two expected nozzle mark locations with detected nozzle marks associated therewith.

2. The method according to claim 1, wherein, said strength score threshold is determined according to the statistics of the strength scores of the selected group of consecutive nozzle marks.

3. A method of identifying at least one malfunctioning nozzle in a digital printing press, said digital printing press including a plurality of nozzles, the method comprising the procedures of:

printing a design on a substrate;
acquiring at least one image of the printed design;
identifying a least one artifact in the acquired image; and
identifying said malfunctioning nozzle and classifying said at least one malfunctioning nozzle according to said at least one of said acquired image of said printed design, at least a portion of a nozzle pattern, and at least a portion of a uniformity pattern, by:

printing at least said portion of said nozzle pattern, said nozzle pattern including a nozzle color pattern for each of least one printed color, each nozzle color pattern including a plurality of nozzle pattern rows, each nozzle pattern row including a plurality of nozzle marks representing samples of 1 in K nozzles, each row shifted by an offset of 1 nozzle, each nozzle pattern row further including at least one nozzle locator;

acquiring an image of the printed portion of said nozzle pattern;

detecting nozzle marks and said at least one nozzle locator in each of said nozzle pattern rows of the respective nozzle color patterns in said portion of said nozzle pattern;

for each nozzle pattern row, determining a grid for a selected group of consecutive nozzle marks including expected nozzle mark locations and actual nozzle mark locations;

associating each expected nozzle mark location with a respective detected nozzle mark and determining the distance between the expected nozzle mark location and the actual nozzle mark location of the respective nozzle mark; and identifying and classifying nozzles according to the expected nozzle mark location on said grid, the actual nozzle mark location on said grid, the at least one nozzle locator, and K, wherein each nozzle locator exhibits a pre-defined shape printed by a predetermined respective set of nozzles.

4. The method according to claim 1, wherein identifying said at least one malfunctioning nozzle and classifying said malfunction according to said at least a portion of said uniformity pattern includes the procedures of:

printing said at least said portion of said uniformity pattern on a substrate, said uniformity pattern including a plurality of color uniformity patterns respective of each color being printed, each one of said color uniformity patterns including a plurality of color uniformity rows, each color uniformity row in each color uniformity pattern associated with a respective different planned ink density level;

acquiring an image of said portion of said uniformity pattern;

identifying color uniformity rows in the acquired image;
determining the relative density of each bin in each color uniformity row, said bin being defined as at least one pixel in the acquired image;

determining required correction for each bin that exhibits a non-uniform relative density.

5. The method according to claim 1, wherein identifying said malfunctioning nozzle according to said at least one acquired image of said printed design includes the sub-procedures of:

turning off each of at least one suspected nozzle;
for each of the at least one turned off suspected nozzle, printing another repetition of said design;
acquiring an image of said other repetition,
wherein, when a change occurs in the acquired image of said other repetition relative to said acquired image, then determining the nozzle that was turned off is not the malfunctioning nozzle,
wherein, when no change occurs in the acquired image of said other repetition, then determining the nozzle that was turned off is a malfunctioning nozzle.

6. The method according to claim 1, wherein identifying said malfunctioning nozzle according to said at least one acquired image of said printed design includes the sub-procedures of:

compensating for at least one suspected nozzle;
for each of the at least one compensated suspected nozzle, printing another repetition of said design;
acquiring an image of said other repetition,
wherein, when no artifacts appear in said other acquired image relative to said acquired image, then determining the malfunctioning nozzle has been identified and compensated for.

7. A method of identifying at least one malfunctioning nozzle in a digital printing press, said digital printing press including a plurality of nozzles, the method comprising the procedures of:

printing a design on a substrate;
acquiring at least one image of the printed design;
identifying at least one artifact in the acquired image;
printing at least one of at least a portion of a nozzle pattern and at least a portion of a uniformity pattern;

acquiring at least one image of said at least one of at least a portion of said nozzle pattern and at least a portion of said uniformity pattern;

identifying said malfunctioning nozzle and classifying a malfunction of said at least one malfunctioning nozzle according to one of said at least one image of the printed design and said at least one acquired image of said at least one of said at least a portion of said nozzle pattern and said at least a portion of said uniformity pattern, wherein said identifying said malfunctioning nozzle and classifying said at least one malfunctioning nozzle according to said at least one image of said printed design includes the sub-procedures of:

turning off at least one suspected nozzle;

for each of the at least one turned off suspected nozzle printing another repetition of said design;

acquiring an image of said other repetition, wherein, when a change occurs in the acquired image of said other repetition relative to said acquired image, then determining the nozzle that was turned off is not the malfunctioning nozzle, wherein, when no change occurs in the acquired image of said other repetition, then determining the nozzle that was turned off is a malfunctioning nozzle.

8. The method according to claim 7, wherein identifying said malfunctioning nozzle according to said at least one acquired image of said printed design includes the sub-procedures of:

compensating at least one suspected nozzle;

for each of the at least one compensated suspected nozzle, printing another repetition of said design;

acquiring an image of said other repetition, wherein, when no artifacts appear in said other acquired image relative to said acquired image, then determining the malfunctioning nozzle has been identified and compensated for.

9. The method according to claim 7, wherein identifying said at least one malfunctioning nozzle and classifying said malfunction according said at least a portion of said nozzle pattern includes the procedures of:

printing at least said portion of said nozzle pattern, said nozzle pattern including a nozzle color pattern for each of at least one printed color, each nozzle color pattern including a plurality of nozzle pattern rows, each nozzle pattern row including a plurality of nozzle marks representing samples of 1 in K nozzles, each row shifted by an offset of 1 nozzle, each nozzle pattern row further including at least one nozzle locator;

acquiring an image of the printed portion of said nozzle pattern;

detecting nozzle marks and said at least one nozzle locator in each said nozzle pattern rows of the respective nozzle color-patterns in said portion of said nozzle pattern;

for each nozzle pattern row, determining a grid for a selected group of consecutive nozzle marks including expected nozzle mark locations and actual nozzle mark locations;

associating each expected nozzle mark location with a respective detected nozzle mark and determining a distance between the expected nozzle mark location and the actual nozzle mark location of the respective nozzle mark;

identifying and classifying nozzles according to the expected nozzle mark location on said grid, the actual nozzle mark location on said grid, the at least one nozzle locator, and K.

10. The method according to claim 9, wherein a nozzle is classified as one of:

intact;

missing;

deviated;

inconsistent; and redundant.

11. The method according to claim 10, wherein nozzle is classified as intact when a nozzle mark is identified in an expected nozzle mark location within a determined tolerance, wherein a nozzle is classified as missing when an expected nozzle mark location is not associated with a detected nozzle mark, wherein a nozzle is classified as deviated when the distance between said actual nozzle mark location and said expected nozzle mark location associated with the detected nozzle mark is above an x-deviation threshold, wherein a nozzle is classified as inconsistent when the respective detected nozzle mark thereof exhibits a strength score below a determined strength score threshold, wherein a nozzle is classified as redundant when a nozzle mark is detected between two expected nozzle mark locations with detected nozzle marks associated therewith.

12. The method according to claim 11, wherein, said strength score threshold is determined according to the statistics of the strength scores of the selected group of consecutive nozzle marks.

13. The method according to claim 9, wherein each nozzle locator exhibits a pre-defined shape printed by a predetermined respective set of nozzles.

14. The method according to claim 7, wherein identifying said at least one malfunctioning nozzle and classifying said malfunction according to said at least a portion of said uniformity pattern includes the procedures of:

printing said at least said portion of said uniformity pattern on a substrate, said uniformity pattern including a plurality of color uniformity patterns respective of each color being printed, each one of said color uniformity patterns including a plurality of color uniformity rows, each color uniformity row in each color uniformity pattern associated with a respective different planned ink density level;

acquiring an image of said portion of said uniformity pattern;

identifying color uniformity rows in the acquired image;

determining the relative density of each bin in each color uniformity row, said bin being defined as at least one pixel in the acquired image;

determining required correction for each bin which exhibits a non-uniform relative density.

15. A method of identifying at least one malfunctioning nozzle in a digital printing press, said digital printing press including a plurality of nozzles, the method comprising the procedures of:

printing a design on a substrate;

acquiring at least one image of the printed design;

identifying at least one artifact in the acquired image;

printing at least one of at least a portion of a nozzle pattern and at least a portion of a uniformity pattern;

acquiring at least one image of said at least one of at least a portion of said nozzle pattern and at least a portion of said uniformity pattern;

identifying said malfunctioning nozzle and classifying said at least one malfunctioning nozzle according to said at least one acquired image of said at least one of said at least a portion of said nozzle pattern and said at least a portion of said uniformity pattern, wherein said identifying said malfunctioning nozzle and classifying said at least one malfunctioning nozzle is performed according to said at least one image of said printed design; and includes the sub-procedures of:

compensating at least one suspected nozzle;

for each of the at least one compensated suspected nozzle printing another repetition of said design;

acquiring an image of said other repetition, wherein, when no artifacts appear in said other acquired image relative to said acquired image, then the malfunctioning nozzle is identified and compensated for.

16. A method of identifying at least one malfunctioning nozzle in a digital printing press, said digital printing press including a plurality of nozzles, the method comprising the procedures of:

printing a design on a substrate;

acquiring at least one image of the printed design;

identifying at least one artifact in the acquired image;

identifying said malfunctioning nozzle and classifying said at least one malfunctioning nozzle according to said at least one image of the printed design, wherein said identifying said malfunctioning nozzle and classifying said at least one malfunctioning nozzle according to said at least one image of said printed design includes the sub-procedures of:

turning off at least one suspected nozzle;

for each of the at least one turned off suspected nozzle printing another repetition of said design;

acquiring an image of said other repetition, wherein when a change occurred in the acquired image of said other repetition, relative to said acquire image, then the nozzle that was turned off is not the malfunctioning nozzle, wherein when no change occurred in the acquired image of said other repetition, then the nozzle that was turned off is determined to be a malfunctioning nozzle.

17. A system for identifying at least one malfunctioning nozzle in a digital printing press, said digital printing press including a plurality of nozzles, the system comprising:

an imager, including an imaging sensor, configured to acquire at least one image of a printed design printed by said digital printing press, said imager further configured to acquire an image of at least a portion of a nozzle pattern printed by said digital printing press, said nozzle pattern including a nozzle color pattern for each of at least one printed color, each nozzle color pattern including a plurality of nozzle pattern rows, each nozzle pattern row including a plurality of nozzle marks representing samples of 1 in K nozzles, each row shifted by an offset of 1 nozzle, each nozzle pattern row further including at least one nozzle locator;

a processor, coupled to said imager, said processor configured to identify at least one artifact in the acquired image of said printed design, said processor further configured to detect, from said acquired image of at least a portion of a nozzle pattern image, nozzle marks and said at least one nozzle locator in each of said nozzle pattern rows of the respective nozzle color patterns in said portion of said nozzle pattern, said processor further configured to determine, for each nozzle pattern row, a grid for a selected group of consecutive nozzle marks including expected nozzle mark locations and actual nozzle mark locations, said processor further configured to associate each expected nozzle mark location with a respective detected nozzle mark and determine a distance between the expected nozzle mark location and the actual nozzle mark location of the respective nozzle mark; and said processor further configured to identify and classify nozzles according to the expected nozzle mark location on said grid, the actual nozzle mark location on said grid, the at least one nozzle locator, and K, said processor configured to classify a nozzle as:

intact when a nozzle mark is identified in an expected nozzle mark location within a determined tolerance, missing when an expected nozzle mark location is not associated with a detected nozzle mark, deviated when the distance between said actual nozzle mark location and said expected nozzle mark location associated with the detected nozzle mark is above an x-deviation threshold, inconsistent when the respective detected nozzle mark thereof exhibits a strength score below a determined strength score threshold, redundant when a nozzle mark is detected between two expected nozzle mark locations having detected nozzle marks associated therewith.

18. The system according to claim 17, wherein said imager is further configured to acquire an image of at least a portion of a uniformity pattern printed by said printing press, said uniformity pattern including a plurality of color uniformity patterns respective of each color being printed, each one of said color uniformity patterns including a plurality of color uniformity rows, each color uniformity row in each color uniformity pattern associated with a respective different planned ink density level, wherein said processor is configured to identify, from said acquired image of at least a portion of said uniformity, pattern, color uniformity rows in the acquired image, wherein said processor is further configured to determine the relative density of each bin in each color uniformity row, said bin being defined as at least one pixel in the acquired image, wherein said processor is further configured to determine a required correction for each bin which exhibits a non-uniform relative density.

* * * * *